United States Patent
Schomaker et al.

(10) Patent No.: US 10,829,719 B2
(45) Date of Patent: Nov. 10, 2020

(54) SODIUM METHYL GLYCINE-N,N-DIACETIC ACID COMPOUND, PROCESS TO PREPARE IT AND USE THEREOF

(71) Applicant: NOURYON CHEMICALS INTERNATIONAL B.V., Arnhem (NL)

(72) Inventors: Elwin Schomaker, Arnhem (NL); Paulus Johannes Cornelis Van Haeren, Arnhem (NL); Martin Heus, Arnhem (NL); Roy Gérard Doppen, Arnhem (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/629,214

(22) PCT Filed: Jul. 3, 2018

(86) PCT No.: PCT/EP2018/067920
§ 371 (c)(1),
(2) Date: Jan. 7, 2020

(87) PCT Pub. No.: WO2019/007944
PCT Pub. Date: Jan. 10, 2019

(65) Prior Publication Data
US 2020/0131455 A1    Apr. 30, 2020

(30) Foreign Application Priority Data
Jul. 7, 2017  (EP) ..................................... 17180158

(51) Int. Cl.
*C11D 3/33* (2006.01)
*C07C 227/42* (2006.01)
*C07C 229/16* (2006.01)

(52) U.S. Cl.
CPC .............. *C11D 3/33* (2013.01); *C07C 227/42* (2013.01); *C07C 229/16* (2013.01); *C07B 2200/13* (2013.01)

(58) Field of Classification Search
CPC ... C07C 229/16; C07C 227/42; C07C 227/40; C11D 3/33
See application file for complete search history.

(56) References Cited

U.S. PATENT DOCUMENTS

| | | | |
|---|---|---|---|
| 8,628,684 B2* | 1/2014 | Mrzena | C07C 227/42 252/182.3 |
| 9,476,013 B2* | 10/2016 | Van Der Eerden | C11D 11/02 |
| 10,421,711 B2* | 9/2019 | Franzke | C11D 3/33 |
| 2012/0046491 A1 | 2/2012 | Mrzena et al. | |
| 2020/0095189 A1* | 3/2020 | Kadam | C07C 229/16 |
| 2020/0181537 A1* | 6/2020 | Reinoso Garcia | C11D 7/3245 |

FOREIGN PATENT DOCUMENTS

| | | | | |
|---|---|---|---|---|
| WO | 2010133618 A1 | 11/2010 | | |
| WO | WO-2010133618 A1 * | 11/2010 | ........... | C07C 227/42 |
| WO | 2012168739 A1 | 12/2012 | | |
| WO | WO-2012168739 A1 * | 12/2012 | ............... | C11D 3/33 |
| WO | 2015173157 A2 | 11/2015 | | |
| WO | WO-2015173157 A2 * | 11/2015 | ........... | C07C 227/42 |
| WO | 2017102483 A1 | 6/2017 | | |
| WO | WO-2017102483 A1 * | 6/2017 | ........... | C07C 227/42 |

OTHER PUBLICATIONS

Solid State Characterization of Pharmaceuticals 63 (R.A. Storey et al., eds., 2011) (Year: 2011).*
A.J. Cruz-Cabeza et al., 44 Chemical Society Reviews, 8619-8635 (2015) (Year: 2015).*
EPO, European Extended Search Report issued in European Patent Application No. 17180158.2, dated Jan. 4, 2018.
EPO, International Search Report and Written Opinion issued in International Application No. PCT/EP2018/067920, dated Oct. 4, 2018.

* cited by examiner

*Primary Examiner* — Alexander R Pagano
(74) *Attorney, Agent, or Firm* — Norris McLaughlin, P.A.

(57) ABSTRACT

A solid composition, methods for preparing and using the composition, and a rehydrated crystal are disclosed. An exemplary solid composition contains at least about 2 wt % of methyl glycine-N,N-diacetic acid trisodium salt of crystal type III, based on the total weight of crystalline methyl glycine-N,N-diacetic acid trisodium salt compounds, wherein the crystal type III is the form of a crystal, comprising a crystalline modification characterized by the reflections enlisted below when analyzed with X-ray diffraction analysis using Cu Kα radiation:

| Type III | |
|---|---|
| 2Θ | d (Å) |
| 5.8 | 15.2 |
| 7.5 | 11.8 |
| 8.1 | 10.9 |
| 9.5 | 9.3 |
| 11.7 | 7.6 |
| 13.9 | 6.4 |
| 15.1 | 5.9 |
| 16.5 | 5.4 |
| 17.3 | 5.1 |
| 18.5 | 4.8 |
| 19.1 | 4.65 |
| 20.1 | 4.4. |

9 Claims, 1 Drawing Sheet

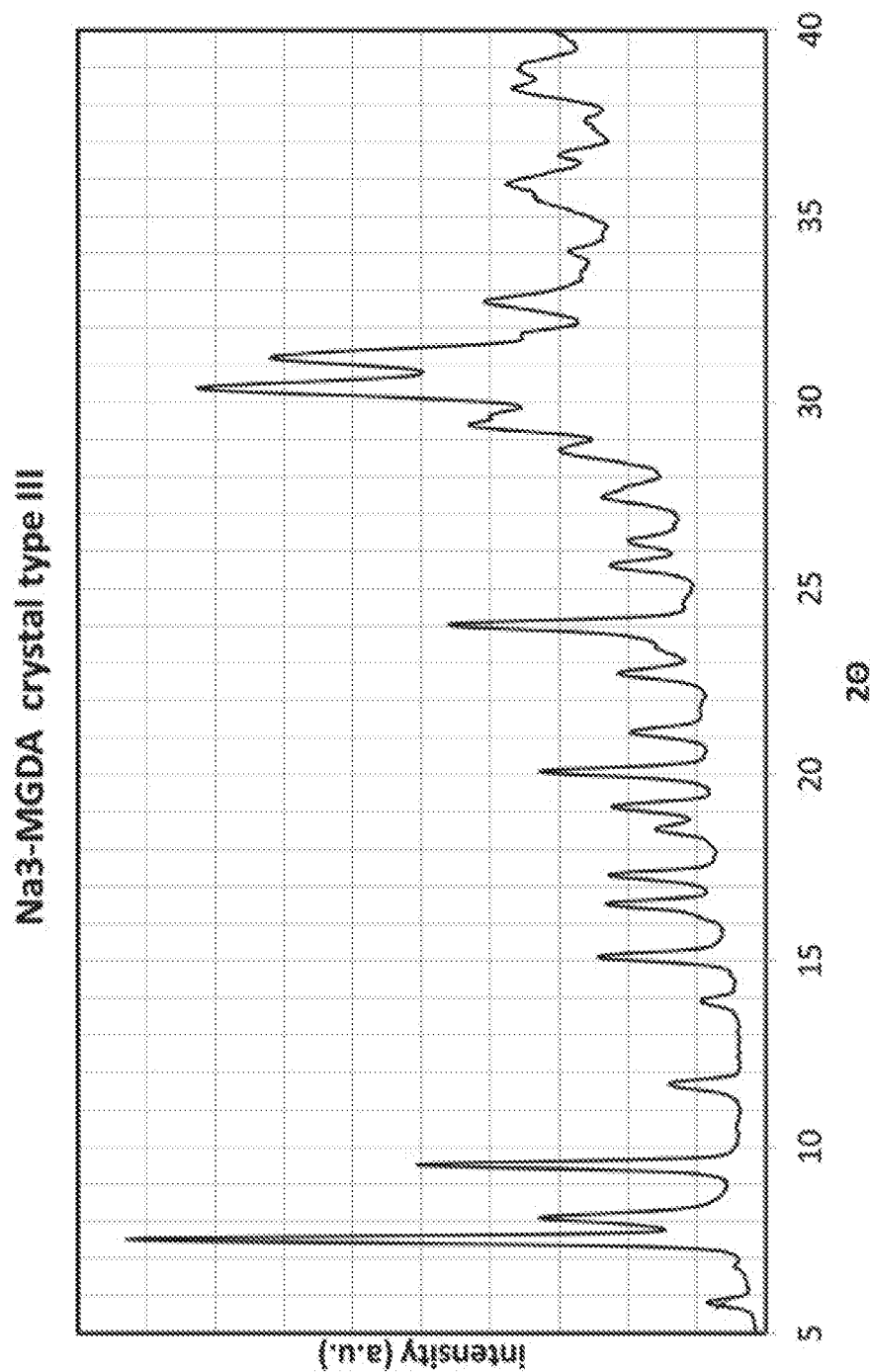
typical diffraction pattern of the new crystal variety (type III). The small reflection marked X is an artefact due to the presence of Cu Kβ -irradiation of the X-ray source

SODIUM METHYL GLYCINE-N,N-DIACETIC ACID COMPOUND, PROCESS TO PREPARE IT AND USE THEREOF

CROSS-REFERENCE TO RELATED APPLICATION

This application is a U.S. National-Stage entry under 35 U.S.C. § 371 based on International Application No. PCT/EP2018/067920, filed Jul. 3, 2018, which was published under PCT Article 21(2) and which claims priority to European Application No. 17180158.2, filed Jul. 7, 2017, which are all hereby incorporated in their entirety by reference.

TECHNICAL FIELD

The present invention relates to a solid methyl glycine-N,N-diacetic acid sodium salt compound in a new crystalline form, to compositions containing the compound, to a process to prepare this compound and to the uses of the compound.

BACKGROUND

Methyl glycine-N,N-diacetic acid and it salts (referred to as MGDA) are known chelating agents having a good biodegradability that are applied in many applications like in detergents, water treatment or as raw material in the production of micronutrients.

One disadvantage of methyl glycine-N,N-diacetic acid and its salts is that when they are isolated as a solid they are relatively sensitive to storage at humid conditions, in which case they absorb water, yielding a tacky material. This makes MGDA of limited suitability for powdery applications, such as in powders that are oftentimes underlying automatic dishwashing (ADW) products, as these powders quickly lose their free-flowing properties.

When isolated as a crystal instead of as an amorphous solid, the free-flowing properties of MGDA can be improved. Two varieties of crystalline Na3-MGDA (the trisodium salt of methyl glycine-N,N-diacetic acid) are known in the art, recognizable via XRD-analysis, yielding different characteristic diffraction patterns.

WO 2010/133618 discloses a process of drying an aqueous solution of Na3-MGDA based on a thin film dryer linked to a paste bunker in which a slurry is ripened. Two different crystal varieties or mixtures of these can be obtained by this process. These crystal varieties can be identified by the d-values in Angstroms correlating to the respective diffraction angles 2 theta in a X-ray powder diffraction pattern as measured using Cu Kα irradiation. The crystal types are referred to as crystal types I and II in this document.

WO2012/168739 discloses a process of spray drying Na3-MGDA starting from a slurry, next agglomerating the obtained solid and subsequently comminuting the obtained agglomerate. The document says that using this process more of the crystalline dihydrate is obtained over the less desired monohydrate. The dihydrate crystal in this document will be referred to as crystal type I and what is called the monohydrate is referred to as crystal type II.

The crystal types I and II can be defined by the below diffraction patterns as given in Table 1.

TABLE 1

| Crystal Type I and II diffraction patterns | | | |
|---|---|---|---|
| type I | | type II | |
| 2Θ | d (Å) | 2Θ | d (Å) |
| 8.2 | 10.8 | 8.4 | 10.5 |
| 10.5 | 8.4 | 9.5 | 9.3 |
| 15.6 | 5.7 | 11.1 | 8 |
| 16.5 | 5.4 | 13.2 | 6.7 |
| 17.1 | 5.2 | 13.9 | 6.4 |
| 18.1 | 4.9 | 15.8 | 5.6 |
| 18.8 | 4.7 | 16.5 | 5.35 |
| 21 | 4.25 | 16.8 | 5.25 |
| 21.4 | 4.15 | 17.3 | 5.1 |
| 22.6 | 3.9 | 17.7 | 5 |
| 23.7 | 3.75 | 18.9 | 4.7 |
| 24.7 | 3.6 | 20.3 | 4.35 |

In WO2012/168739 it is shown that for many applications crystal type I is the preferred variety, as it is less hygroscopic. Powders or granules containing a high degree of crystal type I keep their free-flowing character better upon storage at high humidity conditions, while products containing only or mainly the type II variety fail at these conditions.

There is a continued need in the art for new varieties of the methyl glycine-N,N-diacetic acid chelating agent. Especially there is a need for varieties that have properties that make them more suitable for use in the dry form without caking than the already known varieties. In addition, it is for example known that a too high water content in chelating agents may result in reduced stability of detergent formulations in which they are used because water negatively impacts on bleaching agents, such as for example percarbonates, as often used in detergent formulations together with chelating agents.

BRIEF SUMMARY

A solid composition, methods for preparing and using the composition, and a rehydrated crystal are disclosed. An exemplary solid composition contains at least about 2 wt % of methyl glycine-N,N-diacetic acid trisodium salt of crystal type III, based on the total weight of crystalline methyl glycine-N,N-diacetic acid trisodium salt compounds, wherein the crystal type III is the form of a crystal, comprising a crystalline modification characterized by the reflections enlisted below when analyzed with X-ray diffraction analysis using Cu Kα radiation:

| Type III | |
|---|---|
| 2Θ | d (Å) |
| 5.8 | 15.2 |
| 7.5 | 11.8 |
| 8.1 | 10.9 |
| 9.5 | 9.3 |
| 11.7 | 7.6 |
| 13.9 | 6.4 |
| 15.1 | 5.9 |
| 16.5 | 5.4 |
| 17.3 | 5.1 |
| 18.5 | 4.8 |
| 19.1 | 4.65 |
| 20.1 | 4.4 |

DETAILED DESCRIPTION OF THE DRAWINGS

FIG. 1 is a powder diffractogram.

DETAILED DESCRIPTION

Surprisingly, we have now found that crystal type I compounds can be fully converted into a new crystalline variety, referred to as crystal type III for short in this application, by a conversion of crystal type I or compositions that contain crystal type I.

The present invention provides a solid composition comprising at least 2 wt %, based on the total weight of crystalline methyl glycine-N,N-diacetic acid trisodium salt compounds, of methyl glycine-N,N-diacetic acid trisodium salt in the form of a crystal type III, the crystal type III comprising a crystalline modification characterized by the reflections listed below in Table 2 when analyzed with X-ray diffraction analysis using Cu Kα radiation.

TABLE 2

| Crystal Type III Diffraction pattern Type III | |
|---|---|
| 2Θ | d (Å) |
| 5.8 | 15.2 |
| 7.5 | 11.8 |
| 8.1 | 10.9 |
| 9.5 | 9.3 |
| 11.7 | 7.6 |
| 13.9 | 6.4 |
| 15.1 | 5.9 |
| 16.5 | 5.4 |
| 17.3 | 5.1 |
| 18.5 | 4.8 |
| 19.1 | 4.65 |
| 20.1 | 4.4 |

This new crystal type III can be identified with X-ray diffraction analysis, yielding a list of main characteristic reflections (on using Cu Kα radiation), as summarized above in Table 2 and as exemplified with the powder diffractogram given in FIG. 1. It should be noted that the crystal type III can only be identified if it is present in the composition of the present invention, i.e. in an amount of at least 2 wt %. Preferably the amount of the crystal type III on methyl glycine-N,N-diacetic acid trisodium salt content in the composition is at least 5 wt %, even more preferably at least 10 wt %, and up to 100 wt %

The overall pattern can be described in terms of a unit cell having unit cell parameters in the range of:

a=6.2+/−0.05; b=30.4+/−0.1; c=11.8+/−0.1; β=90.7+/−0.5.

An important advantage of the new variety crystal type III is that it contains significantly less water and hence contains an up to 12% higher content of actives, which is beneficial int. al. when aiming for reduction of transporting costs. Moreover, the strong desire to go for smaller ADW tablets or ADW tablets having the same size but allowing more freedom in formulating with other ingredients before passing the threshold in size or weight is a benefit that is directly related to the higher active ingredient of the new crystal type III.

Surprisingly, it appears that the new crystal type III brings an additional functionality when fast dissolution is needed; e.g when making part of a formulation of dish-washing tablets. The compound of the present invention provides tablet disintegrant functionality, and thereby reduces the need for other disintegrants that are normally used in formulations to speed up the breaking up of the tablets.

The present invention also relates to a process to make the above methyl glycine-N,N-diacetic acid salt of crystal type III and to (further) compositions containing the same.

Accordingly, the present invention provides a process to prepare the methyl glycine-N,N-diacetic acid trisodium salt of crystal type III and compositions containing this crystal type III as covered by the present invention, the process containing a step of subjecting a composition containing methyl glycine-N,N-diacetic acid trisodium salt with a crystalline modification characterized of crystal type I to a heat treatment at a temperature of between 75 and 200° C., a low pressure treatment at a pressure that is between 0 and 1 bar, or to both a heat treatment and a low pressure treatment simultaneously or one after the other.

The above process encompasses the formation of crystal type III starting from crystal type I. It should be realized that this process is not a simple drying process but really a conversion. If the crystal type I is isolated in a relatively wet form, the process will take longer as the conversion into crystal type III will take place after the crystal type I reaches the required dryness. This is noteable from any weight loss that can occur when converting type I to type III being around the above about 12% or visibly more than this 12%. It is hence preferred that the above process is performed starting with crystal type I solids that contain besides crystal water less than 5 wt % of further water, preferably less than 1 wt % of further water, the further water not being crystal water.

It should be noted that the prior art documents WO 2012/168739 and WO 2010/133618 though they do disclose the crystal type I these documents do not disclose any treatment of these type I crystals under conditions that would lead to a clearly analyzable amount of crystal type III as covered by the present invention. In a spray drying process, for example, if heat is applied, such heat treatment is so brief that no detectable amount of crystal type III can be formed.

WO02017/102483 and WO2015/173157 disclose solid MGDA products that undergo a heat treatment that can be considered a heat treatment as described above. However it should be noted that in both these documents any MGDA crystals disclosed are of the crystal type II form (even though in WO2017/102483 the material is called type I, by the diffraction pattern it is visible that it is what we have defined as type II). As demonstrated below, MGDA crystals of type II cannot be converted to the crystal type III of the present invention by a heat treatment.

Upon exposing materials that contain the crystal type III form of methyl glycine-N,N-diacetic acid trisodium salt of the present invention to humid conditions, water vapour, one ends up again with materials containing solely the crystal type I variety wherein compared to the original non-treated material the overall crystallinity is reduced after rehydration, though highly surprisingly these crystal type I-containing compounds (i.e. converted from type I-containing materials into type III and back into type I) retain better free flowability at high humidity conditions than the original non-treated materials.

Thus, the new methyl glycine-N,N-diacetic acid salt of crystal type III can be hydrated to a new version of crystal type I with better free flowing properties, which is also part of the present invention.

The invention provides a process to convert the methyl glycine-N,N-diacetic acid trisodium salt of crystal type III or a composition containing such a methyl glycine-N,N-diacetic acid trisodium salt of crystal type III into a methyl glycine-N,N-diacetic acid trisodium salt of hydrated crystal type I, that is a crystal type I with different properties, by contacting the product of crystal type III with water vapour under conditions of up to 80% relative humidity for a time that is 1 minute to 12 hours. The invention also provides the product of the above process, shortly referred to as the hydrated crystal type I or any composition containing this hydrated crystal type I in at least 2 wt %, or preferably at least 5 wt % or even more preferably at least 10 wt %, and up to 100 wt % on total solids content.

Preferably, the process is done by contacting with water vapour under 40-75 relative humidity, even more preferably 50-70 relative humidity. The process is preferably done at a temperature that is between 0 and 100° C., even more preferably between 20 and 60° C. In yet another preferred embodiment this process is performed for 30 minutes to 6 hours, even more preferred 1 to 3 hours. It is clear to someone skilled in the art that higher relative humidity, higher temperature will make the process faster and that lower humidity and lower temperature will make the process slower.

Finally, the invention relates to uses of the salt of crystal type III, compositions containing this crystal type III and the hydrated crystal type I.

These uses involve the use of any of the compositions containing the methyl glycine-N,N-diacetic acid trisodium salt of crystal type III or of hydrated crystal type I as a component in detergent formulations, such as automatic dishwashing formulations.

The three crystal varieties discussed in this document, i.e. type III of this invention and the state of the art types I and II, have different X-ray diffraction characteristics. For the sake of easily distinguishing between the three types, these are all summarized in Table 3. The diffraction pattern of type III is furthermore attached as FIG. 1.

TABLE 3 first twelve strongest reflections observed for the three different Na$_3$-MGDA crystal varieties (X-ray diffraction 2Θ-values obtained by using Cu Kα irradiation (accuracy: +/− 0.1°). d-values calculated from the 2Θ-values).

| type I | | type II | | type III | |
|---|---|---|---|---|---|
| 2Θ | d (Å) | 2Θ | d (Å) | 2Θ | d (Å) |
| 8.2 | 10.8 | 8.4 | 10.5 | 5.8 | 15.2 |
| 10.5 | 8.4 | 9.5 | 9.3 | 7.5 | 11.8 |
| 15.6 | 5.7 | 11.1 | 8 | 8.1 | 10.9 |
| 16.5 | 5.4 | 13.2 | 6.7 | 9.5 | 9.3 |
| 17.1 | 5.2 | 13.9 | 6.4 | 11.7 | 7.6 |
| 18.1 | 4.9 | 15.8 | 5.6 | 13.9 | 6.4 |
| 18.8 | 4.7 | 16.5 | 5.35 | 15.1 | 5.9 |
| 21 | 4.25 | 16.8 | 5.25 | 16.5 | 5.4 |
| 21.4 | 4.15 | 17.3 | 5.1 | 17.3 | 5.1 |
| 22.6 | 3.9 | 17.7 | 5 | 18.5 | 4.8 |
| 23.7 | 3.75 | 18.9 | 4.7 | 19.1 | 4.65 |
| 24.7 | 3.6 | 20.3 | 4.35 | 20.1 | 4.4 |

Throughout this specification any diffractograms were recorded using a Bruker-AXS D8 reflection-diffractometer with Ni filtered Cu Kα radiation. Generator settings are 40 kV, 40 mA. Divergence and anti-scatter slit V20 (variable 20 mm), detector slit 0.6 mm Measuring range: 2Θ=2.0-70.0°, step size 0.02°, time per step 2.2 seconds.

The degree of crystallinity was ascertained from the X-ray powder diffractograms by determining the surface fraction of the crystalline phase and of the amorphous phase and using this to calculate the degree of crystallinity, CD, as the ratio of the area of the crystalline phase, Ic, to the total area, consisting of the area of the amorphous phase, Ia, and the area of the crystalline phase; degree of crystallinity (%)=Ic/(Ic+Ia)*100.

This procedure was performed using Bruker EVA v.4.0 software with the following parameters: enhancement disabled, curvature 2.5, threshold 1.

The present invention in an embodiment relates to compositions containing methyl glycine-N,N-diacetic acid trisodium salt of crystal type III and less than 50 wt %, preferably 20 wt % of methyl glycine-N,N-diacetic acid trisodium salt in another crystalline modification, based on the total weight of crystalline compounds in the composition. In an even more preferred embodiment these compositions contain less than 10 wt % of another crystalline modification, based on the total weight of crystalline compounds in the composition.

Yet even more preferably, these compositions have a degree of crystallinity of higher than 10%, most preferably higher than 20%.

In embodiments the above compositions can additionally contain a compound selected from the group consisting of another chelating agent, a builder, a surfactant, a descaling agent and an anti-corrosion agent.

The process to prepare the methyl glycine-N,N-diacetic acid trisodium salt of crystal type III of the present invention contains a step of subjecting a composition containing methyl glycine-N,N-diacetic acid trisodium salt with a crystalline modification characterized by the crystal type I reflections to a heat treatment at a temperature of between 75 and 200° C., preferably between 100 and 180° C., even more preferably 140 to 170° C., a low pressure treatment at a pressure that is between 0 and 1 bar, preferably between 0.02 and 0.7 bar, even more preferably 0.05 and 0.5 bar, or to both a heat treatment and a low pressure treatment simultaneously or one after the other.

Preferably, the above heat treatment and/or low pressure treatment is performed for a period between 1 minute and 24 hours, preferably 10 minutes to 10 hours.

In preferred embodiments the above heat treatment or low pressure treatment can be performed in the presence of a drying agent. In further preferred embodiments, if any low pressure is used it is done simultaneously with the heat treatment, or a temperature that can be between 40 and 75° C.

As indicated, the invention additionally relates to a process to convert the Na3-MGDA salt of crystal type III of the invention into a product with a crystalline modification of crystal type I by contacting the crystal type III salt with water vapour.

Though the product obtained has the same crystalline modification as crystal type I already known from the prior art, in its rehydrated form it is characterized by better free flowing properties than the crystal type I used to prepare crystal type III. Consequently, it must be concluded that the rehydrated crystal type I product obtained from the above process in which the crystal type III is hydrated is not the same as original crystal type I as known in the state of the art.

The crystal type III salt of the invention, any composition as disclosed above containing this crystal type III salt of the invention and the rehydrated crystal type I product can all be beneficially used in many applications such as detergent components.

The invention is illustrated by the examples below.

Examples 1-3—Preparation of Na3-MGDA Solids Using A Double Drum Dryer

Na3-MGDA solid samples were prepared by feeding a heated (≠110 C) Na3-MGDA slurry containing seeds of the crystalline variety type I to a double drum dryer. The process conditions and the enantiomeric ratio of the Na3-MGDA samples are summarized in Table 3.

As far as the crystalline fraction of the resulting solid materials is concerned, according to XRD-analysis, these samples only contained crystal variety type I. The crystallinities obtained are summarized in Table 3.

Example 4—Preparation of Na3-MGDA Solids Containing the New Crystal Variety Type III The samples prepared in Example 1 were dried at 160° C. during 1 hour. The weight loss involved was 10±1 wt %.

These dried samples were subsequently subjected to XRD analysis. No traces of crystal variety I or II were found; instead only reflections of the new variety (III) were identified, in conformity with the diffraction pattern as shown in FIG. 1. The crystallinities obtained are summarized in Table 3.

Example 5—Rehydration of Na3-MGDA Solids Containing the New Crystal Variety Type III into A New Form of Crystal Variety Type I The samples that were dried at 160° C. were stored at 40° C. and 75% RH during 3 hrs and subsequently dried in a circulation oven at 50° C. overnight. The samples were again subjected to XRD analysis. All samples showed solely crystalline variety type I. The crystallinities obtained are summarized in Table 4.

Although the crystallinity as measured by XRD analysis was reduced as compared to the original samples, it was concluded that the crystal varieties I and III can be converted into each other by dehydration or rehydration.

| Example # | $T_{drum}$ (° C.) | feed concentration (w % Na3MGDA) | tangential speed drum (m/min) | enantiomeric ratio (D/L) | crystallinity after drum drying (%; type I) | crystallinity after drying at 160° C. (%; type III) | crystallinity after rehydration (%; type I) |
|---|---|---|---|---|---|---|---|
| 1 | 148 | 60 | 4.9 | 50/50 | 60 | 43 | 49 |
| 2 | 149 | 57 | 7.9 | 46/54 | 67 | 50 | 55 |
| 3 | 163 | 60 | 6.1 | 50/50 | 53 | 52 | 42 |

Comparative Example 6—Dehydration of Na3-MGDA Solids Containing Crystal Variety Type II A sample of Trilon M granules (Na3-MGDA solids ex BASF) was analyzed with XRD. The sample appeared to contain solely crystal type variety II. The overall degree of crystallinity was 71%.

These Trilon M granules were dried at 160° C. A sample was taken after 1 hour of drying and analyzed with XRD. Only crystal variety type II was observed and the overall degree of crystallinity was reduced to 49%.

Another sample was taken after 3 hours of drying at 160° C. XRD-analysis showed that the sample had become fully amorphous.

Example 7—Dehydration of Na3-MGDA Solids Containing Crystal Variety Type I at Other Conditions The compound of Example 1 was exposed to various other drying conditions (temperature, pressure, time). Using XRD analysis the conversion of crystal variety type I into crystal variety type III was determined.

From the results as presented in Table 5 it was concluded that the conversion of crystal type I into crystal type III can be performed at various conditions by matching the time scale of the drying treatment to e.g. the temperature and (reduced) pressure.

TABLE 5

| drying condition | Degree of crystallinity (%) | conversion into type III (%) |
|---|---|---|
| 10 min at 140° C. at 1 bar | 58 | 8 |
| 10 min at 160° C. at 1 bar | 44 | 77 |
| 10 min at 180° C. at 1 bar | 41 | 40 |
| 20 hr at 50° C. at 0.05 bar | 45 | 100 |
| 4h hr at 100° C. at 0.05 bar | 43 | 100 |

Examples 8 and 9 and Comparative Example 10

Free flowability of materials that were converted from crystal type I into crystal variety type III and then to crystal type I, compared to non-converted crystal type I compounds and crystal type II compounds The compounds obtained in Examples 1 and 3 were dried 4 hours at 160° C. Subsequently, 5 grams of each sample were distributed evenly over the bottom of a (separate) crystallization dish (diameter 10 cm) and stored for 5 days in a climate chamber at 40° C. and 75% relative humidity. As a reference also the non-treated samples, as well as a sample of Trilon M granules (Na3-MGDA solid ex BASF), were stored in the same climate chamber at the same time.

To improve reliability of the testing, three separate dishes of all samples were stored at the same conditions.

After five days the dishes were weighed and the gain in mass of the contents was determined. The mean results are summarized in Table 6.

To estimate the amount of material that was still free flowing, the dishes were first tapped gently and then were mounted vertically to estimate the amount of material that remained sticking on the glass surface versus the amount of granular material ending on the bottom.

From the results as summarized in Table 6 it was concluded that despite the fact that the treated sampled showed a much larger gain in weight, these samples showed a significantly larger amount of free flowing material as compared to the non-treated materials. Hence although the crystal type III appears to have converted back to crystal type I, still a new product type is obtained that has better free flowing properties.

TABLE 6

| Example | sample# | fraction free flowing (%) Original | fraction free flowing (%) Treated | weight gain (%) Original | weight gain (%) Treated |
|---|---|---|---|---|---|
| 8 | 1 | 40 | 65 | 11 | 27 |
| 9 | 3 | 20 | 80 | 17 | 29 |
| 10 | Trilon M | 0 |  | 30 |  |

Example 11—Formation of Crystal Type III from Crystal Type I and Comparison of Dissolution Properties Granules, according to XRD having a crystallinity of 70%, only showing the crystalline variety type I, were dried overnight at 160° C., yielding granules only showing crystalline variety III (total crystallinity 55%). After this treatment no significant change in particle size distribution was observed.

The dissolution rate of these granules was compared to the dissolution rate of the original granules that were not heat treated:

1 gram of granules was added in one shot to a stirred container filled with 75 gram deionized water, equipped with a conductivity measurement probe. The conductivity of the dispersion was monitored in time. The degree of dissolution was determined by dividing the conductivity by the value finally obtained when the sample was fully dissolved yielding a stable level of conductivity.

In Table 7 the time needed to reach a certain degree of dissolution is given for both granules; showing that the type III containing granules dissolve much faster than the type I containing granules.

(The measurements were done in duplicate yielding the same result)

TABLE 7

Comparison of dissolution of type I and III crystals

| % dissolved | time needed (s) type I | time needed (s) type III |
|---|---|---|
| 75 | 40 | 22 |
| 90 | 110 | 36 |
| 95 | 160 | 45 |
| 100 | 260 | 90 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A solid composition containing at least about 2 wt % of methyl glycine-N,N-diacetic acid trisodium salt of crystal type III, based on the total weight of crystalline methyl glycine-N,N-diacetic acid trisodium salt compounds, wherein the crystal type III is the form of a crystal, comprising a crystalline modification characterized by the reflections enlisted below when analyzed with X-ray diffraction analysis using Cu Kα radiation:

| Type III | |
|---|---|
| 2Θ | d (Å) |
| 5.8 | 15.2 |
| 7.5 | 11.8 |
| 8.1 | 10.9 |
| 9.5 | 9.3 |
| 11.7 | 7.6 |
| 13.9 | 6.4 |
| 15.1 | 5.9 |
| 16.5 | 5.4 |
| 17.3 | 5.1 |
| 18.5 | 4.8 |
| 19.1 | 4.65 |
| 20.1 | 4.4. |

2. The composition containing methyl glycine-N,N-diacetic acid trisodium salt in the form of the crystal type III modification of claim 1 and less than 20 wt % of methyl glycine-N,N-diacetic acid trisodium salt in another crystalline modification, based on the total weight of methyl glycine-N,N-diacetic acid trisodium salt crystalline compounds in the composition.

3. The composition of claim 2 wherein the composition has a degree of crystallinity of higher than 10%.

4. The composition of claim 2 further comprising a compound selected from the group of a chelating agent, a builder, a surfactant, a descaling agent, and an anti-corrosion agent.

5. A method for preparing the composition containing methyl glycine-N,N-diacetic acid trisodium salt of the crystal type III of claim 1, the method comprising:

subjecting a composition containing methyl glycine-N,N-diacetic acid trisodium salt with a crystalline modification characterized by the type I reflections listed below when analyzed with X-ray diffraction analysis using Cu Kα radiation to a heat treatment at a temperature of between about 75 and about 200° C., a low pressure treatment at a pressure that is between 0 and 1 bar, or to both a heat treatment and a low pressure treatment simultaneously or one after the other

| type I | |
| --- | --- |
| 2Θ | d (Å) |
| 8.2 | 10.8 |
| 10.5 | 8.4 |
| 15.6 | 5.7 |
| 16.5 | 5.4 |
| 17.1 | 5.2 |
| 18.1 | 4.9 |
| 18.8 | 4.7 |
| 21 | 4.25 |
| 21.4 | 4.15 |
| 22.6 | 3.9 |
| 23.7 | 3.75 |
| 24.7 | 3.6. |

6. The method of claim 5 wherein the heat treatment and/or low pressure treatment is performed for a period between 1 minute and 24 hours.

7. A method for converting the methyl glycine-N,N-diacetic acid trisodium salt of crystal type III of claim 1 into a methyl glycine-N,N-diacetic acid trisodium salt with a crystalline modification of hydrated crystal type I wherein hydrated crystal type I is characterized by the reflections listed below when analyzed with X-ray diffraction analysis using Cu Kα radiation:

| type I | |
| --- | --- |
| 2Θ | d (Å) |
| 8.2 | 10.8 |
| 10.5 | 8.4 |
| 15.6 | 5.7 |
| 16.5 | 5.4 |
| 17.1 | 5.2 |
| 18.1 | 4.9 |
| 18.8 | 4.7 |
| 21 | 4.25 |
| 21.4 | 4.15 |
| 22.6 | 3.9 |
| 23.7 | 3.75 |
| 24.7 | 3.6 | by contacting the salt of crystal type III with water vapour under conditions of up to 80% relative humidity for a time of about 1 minute to about 12 hours.

8. The method of claim 7, wherein a methyl glycine-N,N-diacetic acid trisodium salt of hydrated crystal type I is obtained.

9. The composition of claim 1, wherein the composition is a detergent component.

* * * * *